United States Patent [19]

Spence et al.

[11] Patent Number: 4,560,824

[45] Date of Patent: Dec. 24, 1985

[54] HEAT BALANCE CONTROL IN CATALYTIC DEHYDROGENATION OF ISOBUTANE

[75] Inventors: David C. Spence, Coopersburg; William A. Schwartz, Fogelsville, both of Pa.

[73] Assignee: Air Products and Chemicals, Inc., Allentown, Pa.

[21] Appl. No.: 731,423

[22] Filed: May 7, 1985

[51] Int. Cl.$^4$ .................................................. C07C 5/38
[52] U.S. Cl. ..................................... 585/662; 585/654
[58] Field of Search .......................... 585/662, 663, 654

[56] References Cited

U.S. PATENT DOCUMENTS

| | | | |
|---|---|---|---|
| 2,419,997 | 5/1947 | Houdry | 585/662 |
| 2,943,067 | 6/1960 | Sieg | 585/662 |
| 3,032,598 | 5/1962 | Stevenson | 585/662 |
| 3,042,729 | 7/1962 | Mulaskey | 585/662 |
| 3,340,321 | 9/1967 | Craig | 585/662 |
| 3,346,658 | 10/1967 | Mulaskey et al. | 585/662 |
| 3,479,416 | 11/1969 | Tschopp et al. | 585/662 |
| 3,711,569 | 1/1973 | Tschopp et al. | 585/662 |
| 3,780,129 | 12/1973 | Friedrich | 585/662 |
| 4,409,417 | 10/1983 | Herbstman | 585/654 |

*Primary Examiner*—D. E. Gantz
*Assistant Examiner*—A. Pal
*Attorney, Agent, or Firm*—Russell L. Brewer; E. Eugene Innis; James C. Simmons

[57] ABSTRACT

This invention relates to an improvement in a process for producing isobutylene by the cyclic, adiabatic dehydrogenation of isobutane. The improvement resides in diluting an isobutane feed stream with n-butane in an amount from about 3-7% by volume and recycling unreacted products plus nC$_4$ unsaturates from the dehydrogenation zone. Additional coke is made by virtue of the use of n-butane and recycle to permit lower feed input temperature.

3 Claims, No Drawings

HEAT BALANCE CONTROL IN CATALYTIC DEHYDROGENATION OF ISOBUTANE

TECHNICAL FIELD

This invention pertains to a process for maintaining heat control within a dehydrogenation zone for the dehydrogenation of isobutane.

BACKGROUND OF THE INVENTION

The catalytic conversion of hydrocarbons by a cyclic, generally adiabatic process, is known. Examples of hydrocarbons which are converted by these processes include the lower paraffins such as propane, n-butane, isobutane, normal and isopentane. Representative products resulting from this process include propylene, butene and butadiene, isobutene; isoamylene and isoprene. In the cyclic catalytic process, conversion of the saturated paraffin is carried out in an endothermic dehydrogenation reaction followed by an exothermic regeneration of the catalyst wherein carbonaceous deposits formed on the catalyst's surface during the hydrocarbon on-stream period are burned thereby furnishing heat required in the catalytic dehydrogenation reaction. To operate, the heat required in effecting dehydrogenation must be equal to the heat provided by the exothermic regeneration as well as other sources of heat input such as sensible heat of feed and air. Representative patents which disclose cyclic, adiabatic catalytic dehydrogenation processes for the production of olefinic materials include:

U.S. Pat. No. 2,419,997, which discloses the production of dehydrogenated aliphatic hydrocarbons in the presence of a chromia-alumina catalyst. A cyclic, generally adiabatic process, is used. A balanced heat load is achieved through the regulation of temperature or time of contact, or both, within the catalytic dehydrogenation reactor to produce a net exothermic heat value while maintaining temperature in a suitable range for dehydrogenation.

U.S. Pat. No. 2,943,067 discloses a process for catalytically dehydrogenating olefins in a cyclic, generally adiabatic process. A chromia-alumina catalyst promoted with a potassium or lithium oxide is used. The catalyst is described as being one giving good conversion and high selectivity over long periods of time. It is stated in the patent the process requires an over-all zero net heat, i.e., the endothermic reaction heat of dehydrogenation must equal the exothermic regeneration heat of coke combustion and other sources of heat input in order to avoid a runaway reaction.

U.S. Pat. No. 3,780,129 discloses a process for the dehydrogenation of aliphatic hydrocarbons to produce diolefins, the process utilizing a chromia-alumina catalyst in a cyclic, adiabatic process.

U.S. Pat. No. 3,340,321 discloses a mechanism for temperature control in a process for the dehydrogenation of aliphatic hydrocarbons to produce olefins. Temperature control is maintained by determining the coke requirement for a heat-balanced operation in the production of double bond compounds and controlling the amount of steam introduced into the bed to balance the heat load.

SUMMARY OF THE INVENTION

This invention pertains to a process for producing isobutylene by the dehydrogenation of isobutane while minimizing energy input to the dehydrogenation zone particularly in the form of reduced feed temperature which initially comprises diluting the isobutane feed to the dehydrogenation zone with n-butane and then dehydrogenating. The unreacted material plus n-butylene and butadiene produced in the dehydrogenation zone is then separated from the isobutylene product and recycled back to the dehydrogenation zone. By adjusting the quantity of n-butane to the system, one can produce the desired amount of coke in the dehydrogenation zone to permit increased heat levels to the dehydrogenation zone without an increase in temperature of the feed or air flow.

DETAILED DESCRIPTION OF THE INVENTION

The dehydrogenation of isobutane to form isobutylene is commonly carried out as a cyclic, adiabatic operation, generally involving a plurality of reactors operated in time sequence. In this process, the heat required for the endothermic hydrocarbon conversion is substantially in balance with the exothermic heat derived from the combustion during catalyst regeneration of coke formed on the catalyst. One of the problems of maintaining adiabatic operation in the preparation of isobutylene is that the feed to the dehydrogenation zone typically contains about 98% by volume isobutane or greater and coke production is quite limited. As a result, the feed and/or air temperature to the dehydrogenation zone must be increased or the air input increased to maintain a proper heat balance. This is a considerable expense in view of the fact that only a portion of additional heat required to preheat feed and air is recovered as usable energy.

It has been found that in the dehydrogenation of isobutane where the isobutane content is about 98% by volume or greater, one can reduce the feed temperature to the reactor while maintaining a desired catalytic bed temperature by diluting the feed with n-butane within a range of 3-7% by volume. This level of n-butane is passed through the dehydrogenation zone and the unreacted product plus n-butylene and butadiene produced in the dehydrogenation zone is separated from the isobutylene product. When the unreacted products and nC$_4$ unsaturates are recycled to the dehydrogenation zone, additional coke is generated in the catalyst bed which permits operation of the unit.

Catalysts suited for practicing the invention include conventional dehydrogenation catalysts such as set forth in U.S. Pat. Nos. 3,780,129 and 2,943,067, such catalysts being incorporated by reference. Typically, these are chromia-aluminum catalysts promoted with alkali metal oxides.

The temperature during the dehydrogenation generally will range from about 950° to about 1300° F. with pressures from sub-atmospheric to superatmospheric, e.g. up to about 100 psig. Preferred inlet feed temperatures are from about 1050°–1200° F. The reaction is carried out in a fixed bed catalytic reactor and the space velocity (LHSV) is generally from about 0.15 to about 5 hours$^{-1}$.

The following examples are provided to illustrate embodiments of the invention and are not intended to restrict the scope thereof.

EXAMPLE 1

A cyclic, adiabatic process for the dehydrogenation of isobutane to isobutylene was accomplished using a commercial process and commercial catalysts sold under the trademark CATOFIN by Air Products and Chemicals, Inc. The catalyst used was chromia-alumina catalyst promoted with alkali metal oxide. A hydrocarbon fresh feed consisting essentially of isobutane obtained by the distillation of a mixture of iso and normal butane containing about 2% n-butane. Reactor conditions are represented as follows:

| Fresh Feed Composition | Wt. % |
|---|---|
| Isobutane | 98 |
| n-butane | 2 |

| Catofin Reactor | Temperature °F. |
|---|---|
| Reactor Feed | 1110° F. |
| Regeneration Air Inlet | 1160° F. |
| Average Bed Temperature | 1033° F. |
| Bottom Bed Temperature | 1013° F. |
| Coke Production | 0.8 lbs per 100 lbs of feed |
| Isobutane conversion per pass | 62 |
| Isobutylene selectivity | 91.9% |

EXAMPLE 2

The process of Example 1 was repeated, except that the fresh feed composition was diluted with n-butane, and the reaction product reseparated and unreacted material plus nC4 unsaturates recycled to the dehydrogenation zone. The reaction conditions and product analysis are as follows:

| Fresh Feed Composition | Wt. % |
|---|---|
| Isobutane | 96 |
| n-butane | 4 |

| Catofin Reactor | Temperature °F. |
|---|---|

| -continued | |
|---|---|
| Reactor Feed | 1106° F. |
| Regeneration Air Inlet | 1156° F. |
| Average Bed Temperature | 1043° F. |
| Bottom Bed Temperature | 1033° F. |
| Coke Production | 1.2 lbs per 100 lbs of feed |
| Isobutane conversion per pass | 65.3 |
| Isobutylene selectivity | 92.2% |

The results in Example 2 show that a hydrocarbon feed temperature of 4° F. lower than Example 1 could be utilized to maintain the desired heat balance while also maintaining an average bed temperature of approximately 10° F. higher than in Example 1. As a result, the isobutane conversion per pass increased from 62 to 65% while selectivity remained essentially the same.

What is claimed is:

1. In an adiabatic, cyclic fixed bed catalytic process for the production of isobutylene by the catalytic dehydrogenation of isobutane containing at least 98% isobutane by volume, separating the isobutylene from unreacted isobutane and recycling the unreacted material to the catalytic reactor, the improvement for generating heat within the catalytic reactor which comprises:
   diluting the incoming fresh feed with n-butane to a concentration of from about 3–7% by weight of the feed; and adjusting the concentration of n-butane within the range of from 3–7% to produce a recycle feed having sufficient butadiene therein to produce additional coke within said dehydrogenation zone and thereby obtain a net heat balance of approximately zero.

2. The process of claim 1 wherein the dehydrogenation is carried out in the presence of a chromia-alumina catalyst.

3. The process of claim 1 wherein the inlet temperature of the reactant to the catalytic dehydrogenation zone is from about 1050°–1200° F.

* * * * *